(12) United States Patent
Diana

(10) Patent No.: US 6,565,593 B2
(45) Date of Patent: May 20, 2003

(54) PERIPHERAL VEIN DILATION DEVICE AND METHOD

(76) Inventor: Lawrence G. Diana, 2807 Santa Teresa Rd., Dallas, TX (US) 75218

(*) Notice: Subject to any disclaimer, the term of this patent is extended or adjusted under 35 U.S.C. 154(b) by 24 days.

(21) Appl. No.: 09/802,930

(22) Filed: Mar. 12, 2001

(65) Prior Publication Data

US 2002/0128699 A1 Sep. 12, 2002

(51) Int. Cl.[7] .................................................. A61F 7/00
(52) U.S. Cl. ..................... 607/108; 607/104; 607/114; 607/96
(58) Field of Search ................................. 607/108, 104, 607/107, 109, 110, 111, 112, 114, 96, 98, 99

(56) References Cited

U.S. PATENT DOCUMENTS 4,648,392 A * 3/1987 Cartier et al. ............... 601/151
5,074,285 A * 12/1991 Wright ........................ 601/15
5,683,438 A * 11/1997 Grahn ......................... 126/204

* cited by examiner

*Primary Examiner*—Harold Joyce
(74) *Attorney, Agent, or Firm*—Fitzpatrick, Cella, Harper & Scinto

(57) ABSTRACT

A device suitable for vein dilation includes a chamber having an interior for receiving a portion of a body, and having at least one inlet for admitting a fluid into the chamber. A fluid supply is connected to that inlet to enable the fluid to be admitted into the chamber. A suction source is connected to the chamber such as to be able to apply suction to the interior of the chamber, and a heater is positioned to be able to heat the fluid being supplied to the chamber by the fluid supply. In use, a portion of a body may be massaged and heated (one possibility is to use a fluidized bed formed in the chamber while the body portion is in the chamber), and a vacuum is applied to the portion of the body after performance of the massaging and heating step. Alternatively, the massaging may be omitted, and the body portion heated first and then subjected to a period of suction.

10 Claims, 4 Drawing Sheets

PERIPHERAL VEIN DILATION DEVICE AND METHOD

BACKGROUND OF THE INVENTION

1. Field of the Invention

This invention relates generally to devices and methods for facilitating intravenous access, and in particular to such devices and methods utilizing various combinations of vacuum, heat and tactile stimulation to dilate peripheral veins and thereby to facilitate their identification for blood sampling or cannulation. Other applications of the present invention, however, are also possible, and are within the scope of what the inventor regards as his invention.

2. Related Background Art

Peripheral intravenous access plays an integral role in treatment of patients with both critical and non-critical conditions. It is routinely accomplished by application of a tourniquet to an extremity with enough pressure to occlude venous drainage, but not arterial inflow, thereby causing dilation of veins distal to the tourniquet. Once a dilated vessel is identified, a cannula is inserted percutaneously. Not infrequently, underlying physiologic states including, but not limited to, dehydration, shock from blood loss or redistribution of blood volume, hypothermia, and even anxiety cause peripheral vasoconstriction by neuroendocrine pathways. This vasoconstriction often impedes the normal venous dilation when a tourniquet is applied, making intravenous access problematic. At this point, medical specialists will often apply heat or tactile stimulation, or place the extremity lower than the heart in an attempt to improve peripheral blood flow and overcome vasoconstriction. More central access, with its greater inherent risk to the patient, is often needed if these efforts fail.

Various efforts have been made to ameliorate these problems. U.S. Pat. No. 4,299,219 (Norris, Jr.) relates to a device to dilate peripheral veins at the site of application of the device. Suction from the device is created by an operator-activated plunger. The utility of the device appears to be limited by at least two factors: (1) its usefulness presupposes that a target vein can be identified prior to application of the device; and (2) the device only causes a small area of venodilation, which will rapidly collapse on needle entry.

U.S. Pat. No. 4,747,409 (Silen) relates to a sleeve with heating elements used to enwrap a distal extremity for the purpose of warming, thereby enhancing arterial blood flow. This device would seem to have limited ability to counteract vasoconstriction on the venous side of the circulation.

U.S. Pat. No. 5,074,285 (Wright) relates to one of a number of known devices for applying a thermal environment to an extremity in the hope of achieving various therapeutic effects. An extremity is placed within a stocking that has pockets placed along its length. Thermal elements are then placed in one or more of the pockets, with the intent of applying heat or cold at one or more specified sites along the extremity. This device also incorporates a series of compartments placed along the length of a tubular body that encases the extremity and stocking with the purpose of applying a pressure gradient along the length of the tubular body. The sequenced pressure gradient is used primarily in treating lymphatic or venous stasis problems in extremities requiring thermal therapy.

U.S. Pat. No. 5,441,477 (Hargest) relates to an apparatus combining electrotherapy and the massaging action of a thermally energized fluidized bed for treating injured extremities. (Other patents also relate to the use of a fluidized bed for massaging a part of a body, with or without heating or cooling, e.g., U.S. Pat. No. 4,214,576 (Henley).)

U.S. Pat. No. 5,683,438 (Grahn) relates to a device that combines a heat source with a sustained vacuum to dilate superficial capillary beds with the intent of treating hypothermia.

SUMMARY OF THE PRESENT INVENTION

It is an object of the present invention to provide a device and method that enable reliable dilation of veins and their subsequent identification and access for venipuncture or the like.

According to one aspect of the present invention, this object is attained by providing a device which includes a chamber having an interior for receiving a portion of a body, and having at least one inlet for admitting a fluid into the chamber. A fluid supply is connected to the inlet to enable the fluid to be admitted into the chamber. A heater is positioned so as to be able to heat the fluid being supplied to the chamber by the fluid supply. A suction source is connected to the chamber in such manner as to enable application of suction to the interior of the chamber. The chamber may contain particulate matter such that supply of the fluid into the chamber produces a fluidized bed. The chamber preferably contains a partition or sleeve that divides the chamber into two portions, one of which receives an extremity of a patient's body while the other receives the fluid.

Another aspect of the invention is a method of vasodilation, in which a portion of a body is heated (for example, by means of a fluidized bed), and a vacuum is applied to the portion of the body for a period of time after performance of the heating step. In one embodiment, the heating step may also include massaging of the portion of the body.

These and other objects, features and advantages of the present invention will be more fully appreciated from a consideration of the following detailed description of the preferred embodiments, taken together with the accompanying drawings.

DETAILED DESCRIPTION OF THE PREFERRED EMBODIMENTS

Figure 1:
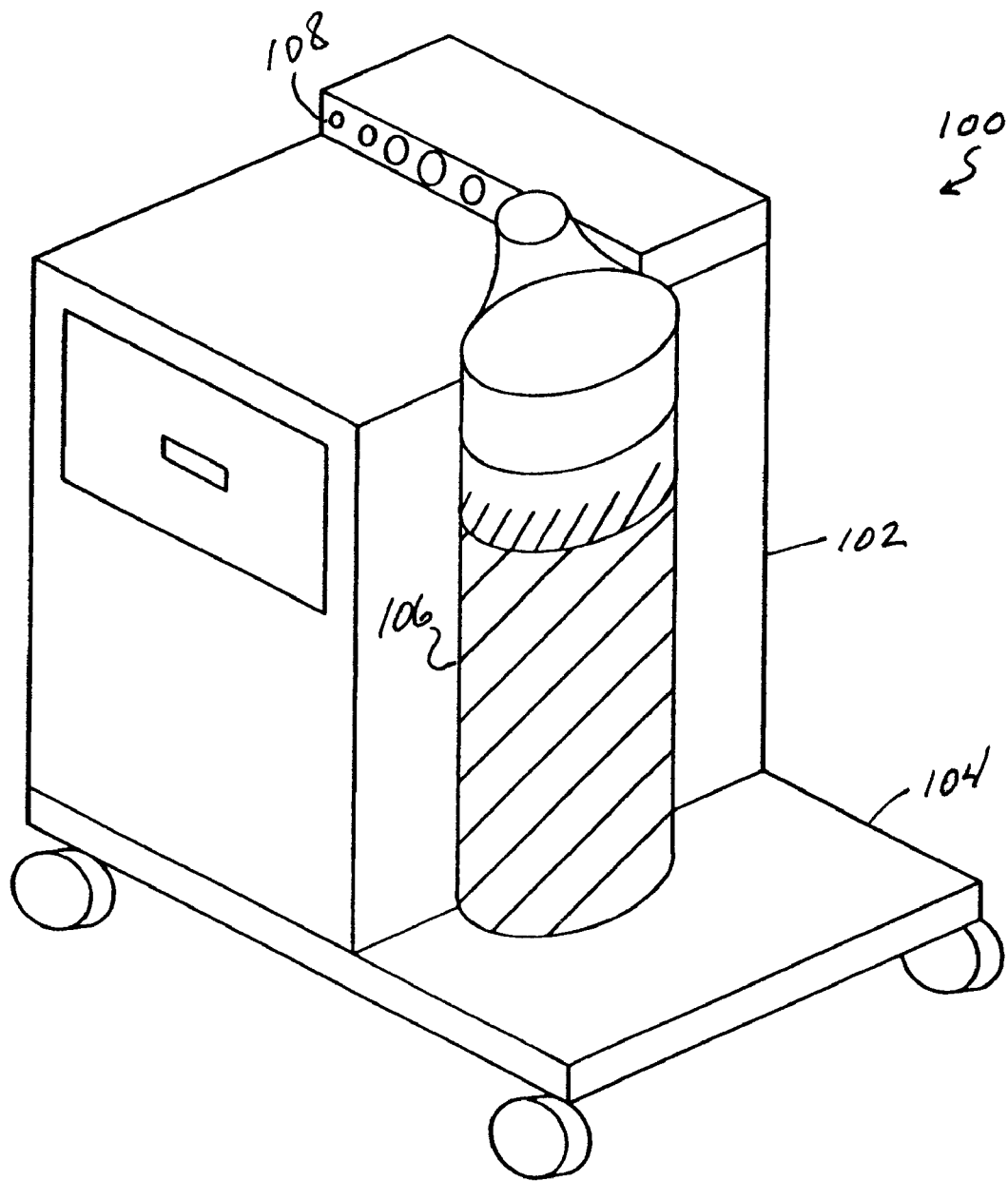
FIG. 1 is a perspective view of a preferred embodiment of an apparatus according to the present invention.

In the embodiment shown in FIG. 1, apparatus 100 includes a cabinet 102 mounted on a cart 104 for mobility (in the version illustrated, the cart 104 is a platform on wheels or castors). Also disposed on the cart 104 is a tubular assembly 106, which is shown as being mounted on the side of the cabinet 102. A control panel 108 is on the top of the cabinet 102.

Figure 2:
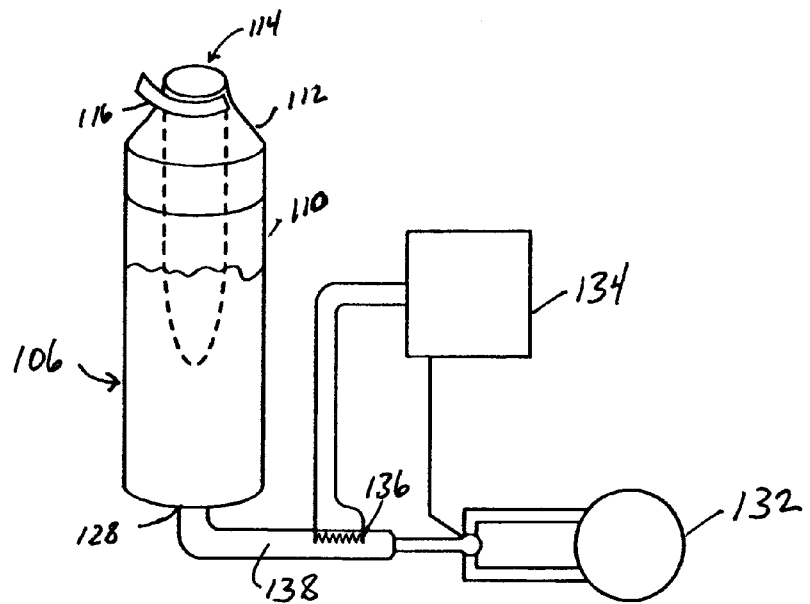
FIG. 2 is a schematic view of the embodiment of FIG. 1, showing more clearly the functional relation of its components.
Figure 3:
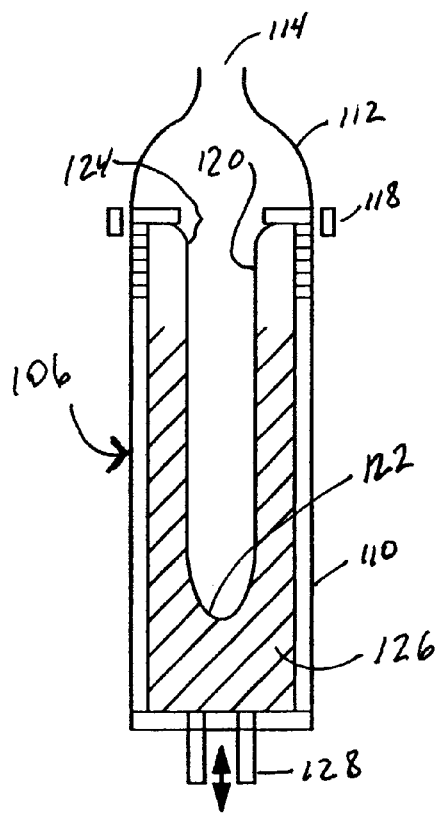
FIG. 3 is a cross-sectional view of a portion of the embodiment of FIG. 1.

As shown in detail in FIGS. 2 and 3, the tubular assembly 106 has a cylindrical housing or outer shell 110, and a cuff 112 of latex rubber mounted airtightly at the upper end of the housing 110. The upper end 114 of the cuff 112 is open, and is of a size suitable for receiving a portion of a patient's body, typically an arm or a leg. The upper, free end 114 of the cuff 112 is provided with a tourniquet arrangement 116 or the like that permits the formation and maintenance of an airtight seal about the periphery of the portion of the patient's body extending into the chamber defined by the interior of the housing 110. In the embodiment shown, the cuff 112 is attached to the cylindrical housing 110 by a clamp assembly 118. The clamp assembly 118 also airtightly secures a tubular plastic barrier or partition 120 in the form of a sleeve, closed at its lower end 122, which is disposed inside the cylindrical housing 110, and open at its upper end 124. In use, the interior of this sleeve or barrier 120 receives a portion of the patient's body.

The tubular housing 110 also may contain a mass of particulate material 126, such as plastic or glass beads, capable of being made into a fluidized bed by the introduction of a sufficient stream of a gas. This particulate material 126 is between the tubular housing 110 and the sleeve 120, and is separated by the latter from the open end of the housing 110. At the bottom end of the tubular housing 110 is a fixture 128 via which a gas, such as air, can be introduced to fluidize the particulate material 126.

In addition, the tubular housing 110 is provided in this embodiment with a suitable number of (one or more) one-way ventholes or valves 130, which can advantageously be perforations in the sleeve 120, each covered with its own small flap of material (which may advantageously be similar or identical to the material of the sleeve itself). These valves permit fluid to leave the tubular housing 110 during fluidization of the particulate matter 126.

As can be seen from FIG. 2, the gas supply fixture 128 at the bottom of the tubular housing 110 is connected to both a blower and a vacuum pump. (These can be the same element 132, as illustrated, since neither the quantity or force of the stream of blown air, nor the suction required to operate the apparatus in the intended manner, is particularly great, and it is not necessary to produce a vacuum at the same time as a stream of blown air is being provided; even though a single pneumatic unit of this type is shown, and is within the scope of the invention, however, reference will be made herein to a "blower" and a "vacuum pump", for simplicity.) When the blower 132 is operating to supply air to the tubular housing 110 to fluidize the particulate matter 126, the control unit 134 receives a signal from a heat sensor, preferably a thermistor (not shown), located at an appropriate position, and uses a feedback loop to control a heating element 136 located in the gas supply line 138 leading from the blower 132 to the tubular housing 110, to maintain the blown air at a desired temperature. Preferably, this temperature can be selected by the physician within some limits.

The operation of this apparatus according to the method of the present invention is as follows.

A portion of a patient's body, such as an arm or a leg, is inserted through the open end 114 of the cuff 112 into the interior of the sleeve 120, and the tourniquet assembly 116 is used to seal the cuff 112 airtightly against the patient's skin. The blower 132 is actuated, as is the heating element 136 in the gas supply line 138, thus providing a flow of warmed gas (air, in the embodiment of FIG. 1) into the tubular housing 110. This supply of gas is delivered under conditions suitable to fluidize the particulate material 126 (if any) in the tubular housing 110, producing (in such case) a fluidized bed in the latter. Motion of the particles in the fluidized bed is transmitted through the sleeve 120 to the patient's skin, providing a massaging action to the latter (in the absence of particulate material, there is simply a pressure on the skin due to the inflow of the gas). At the same time, the warmth of the gas heats the patient's limb.

After a predetermined length of time, the control unit 134 turns off both the heating element 136 and the blower 132, and actuates the vacuum pump 132. (Where, as shown, the blower and vacuum pump are the same element 132, this action involves simply the deactivation of the heating element 136 and the reversal of direction of the action of the pneumatic unit 132). A weak vacuum is then drawn on the interior of the tubular housing 110. This suction forces the one-way valve(s) 130 closed. Because of this, and because the patient's limb is airtightly sealed in the opening of the cuff by the tourniquet assembly 116, the air pressure in the interior of the sleeve 120 is also reduced below ambient atmospheric pressure, thus applying a mild suction to the patient's skin. The fluidized bed action (if provided) suffices to drive some air our through the cuff 112 even through the otherwise airtight seal. (It is nonetheless within the scope of the invention for the sleeve 120 to be elastic enough to distend in response to the drop in pressure, rather than air being forced out through the seal.) The inventor has found that this combination of mild pressurization with heating, followed by mild suction, produces an advantageous and unexpectedly effective vasodilation in the portion of the patient's body so treated. In the case where a fluidized bed is used, the massaging action also contributes to this effect.

The exact length of time for each phase can be controlled automatically, or can be varied by the attending physician as deemed appropriate for the particular patient. A time of a few minutes for each phase may be appropriate. The air may usefully be heated to about 102–104° F. during the heating and massaging phase, and the vacuum drawn during the following phase may be on the order of 2 psi, although this value may be suitably varied by as much as 50% in either direction.

Figure 4:
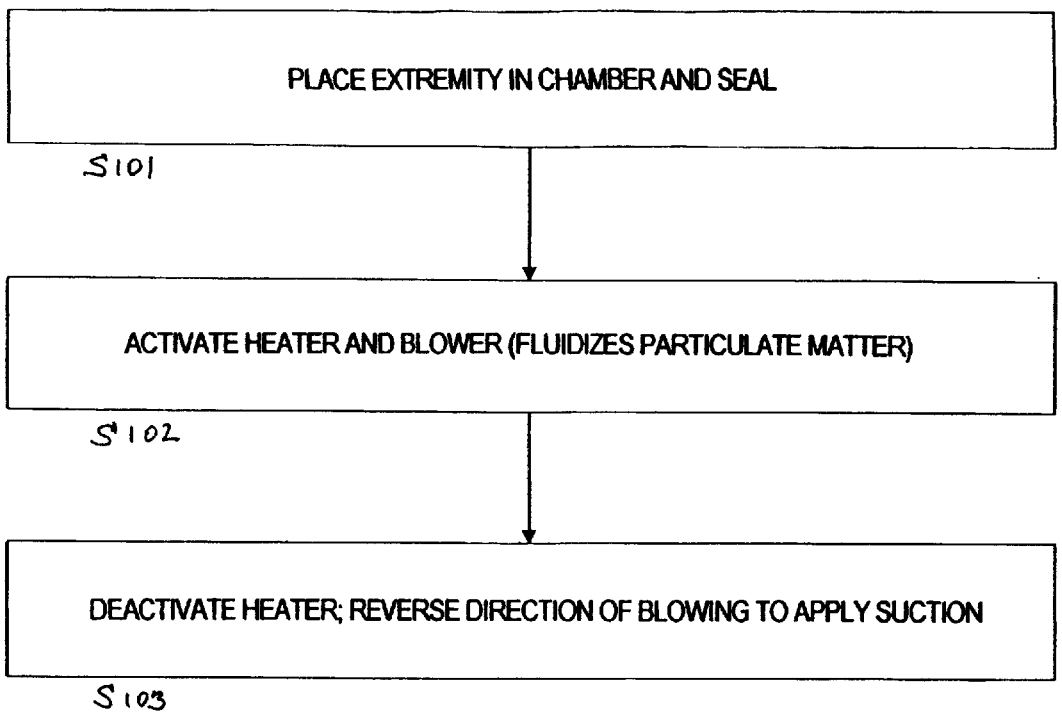
FIG. 4 is a flowchart illustrating a method of using the embodiment of FIG. 1, in accordance with the invention.
Figure 6:
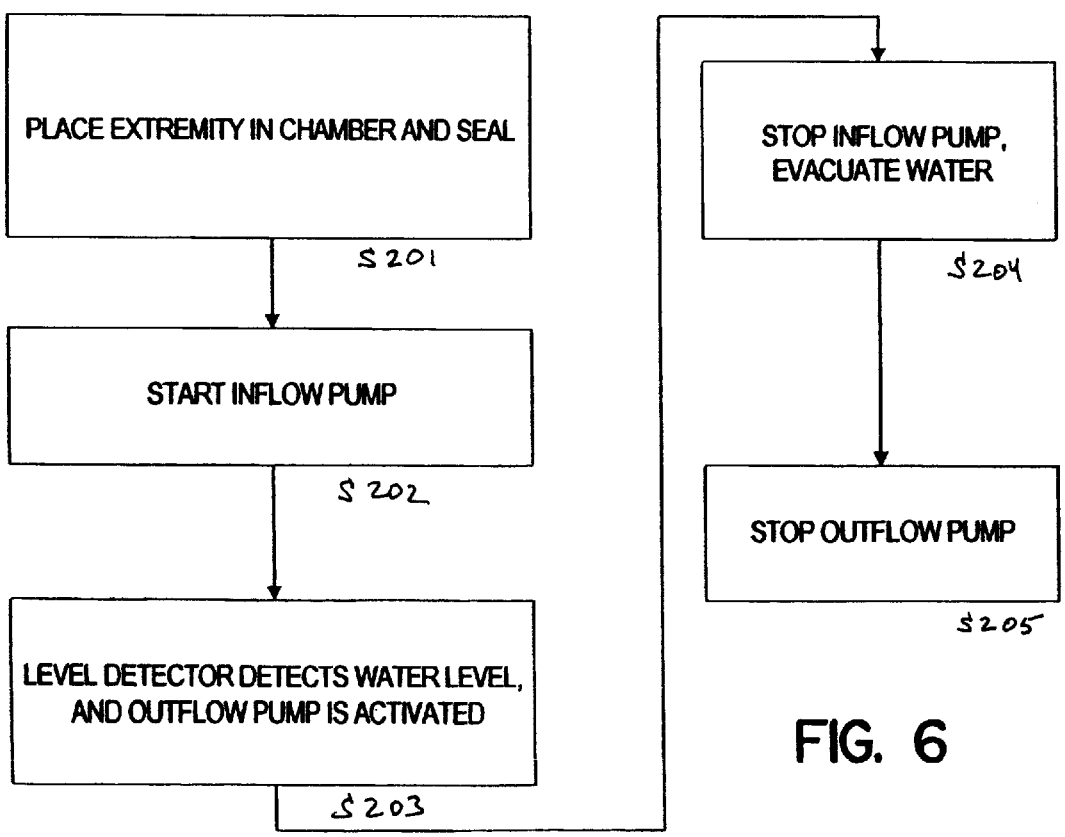
FIG. 6 is a flowchart illustrating a method of using the embodiment of FIG. 5, in accordance with the invention.

One manner of operation of the embodiment of FIGS. 1–3 is illustrated in the flowchart of FIG. 4. As is shown there, in step S101, the portion of the patient's body to be treated (for example, an arm) is placed in the chamber inside the sleeve 120, and an airtight seal between the cuff 112 and the arm is effected. Then, in step S102, the heater 136 and the blower 132 are activated, resulting in the fluidization of the particles 126 (if such are provided) in the housing 110, and in the delivery of both pressure and heat to the arm, with a massaging effect if particles 126 are used. After the passage of a predetermined amount of time during which the arm is subjected to this action, the heater 136 is turned off and the direction of action of the blower 132 is reversed (step S103), to pull a slight vacuum on the air in the housing 110. Since this reduces the air pressure in the sleeve 120 as well, the arm is also subjected to the slight vacuum. This condition is also maintained for a predetermined length of time, which may or may not be the same length as the duration of the warming treatment, and is then terminated. After this, the patient's arm may be withdrawn from the apparatus to see if an appropriate site for venipuncture now exists. If the attending physician deems it appropriate, the process, including steps S101–S103, may be repeated.

Figure 5:
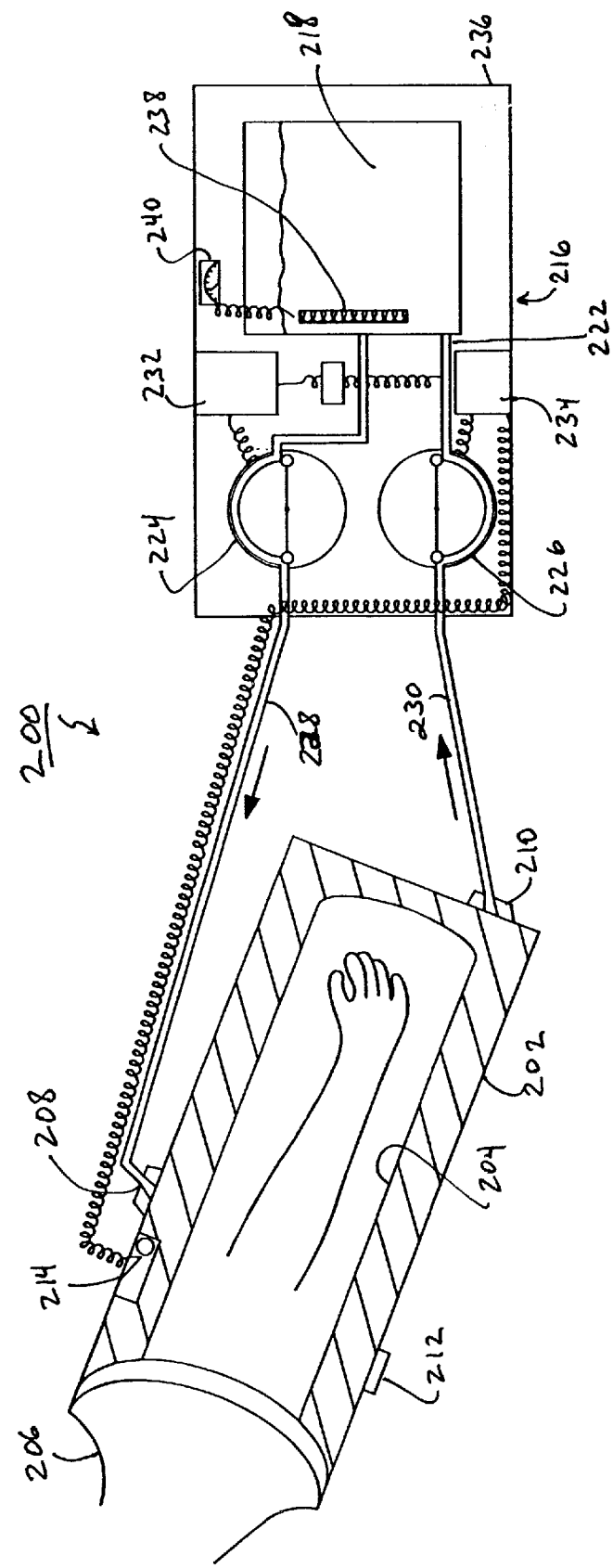
FIG. 5 is a view, partly in section, of another preferred embodiment of an apparatus according to the present invention.

FIG. 5 illustrates a second preferred embodiment 200 of the invention, in which the fluidized bed optionally provided in of the first embodiment 100 is eliminated. In this embodiment, a rigid or semi-rigid outer shell 202 is provided, which contains a flexible, heat-permeable inner liner 204 and has a flexible flange 206 at one end. Gaskets (not shown) attach the flange 206 and the inner liner 204 airtightly to the shell 202. The shell 202 is sufficiently rigid to maintain its shape even in the presence of a small pressure differential across its thickness, such as a differential of 2 psi. The inner liner 204, in contrast, is preferably so light that it will collapse under any significant pressure differential at all (many plastics may be suitable for use as the liner).

The shell 202 has an inlet 208 and an outlet 210 for a fluid, which in this preferred embodiment is water. A pressure-relief valve 212 is provided in one wall of the shell 202, and is constructed to open to allow ambient air into the shell 202 whenever the pressure inside the shell 20 is less than ambient pressure by more than a predetermined amount (say, 80 mm of Hg). Also, toward the top of the shell 202 is provided a fluid-level detector 214, to detect when the level of water in the shell 202 has reached the position of the detector 214, and to send a signal to that effect to a control unit 216 in response to such detection. One simple construction (not shown) of such a detector may be a wire cage provided on the interior of the shell 202, with an electrically conductive float that, upon the water level rising sufficiently, moves into conductive contact with two electrical terminals or contacts to complete an electrical circuit, thereby to allow emission of an electrical signal to the control unit. Other constructions, within the reach of those of ordinary skill, can be used instead. The power for such signal may be provided either by battery at the shell 202, or be supplied from elsewhere.

A reservoir 218 of water is provided, the interior of which communicates via two lines 220 and 222 with two pumps 224 and 226, which may preferably be roller pumps. Each of these pumps 224 and 226 communicates via a respective second line 228 and 230 with either the inlet 208 or the outlet 210, respectively, at the shell 202. Each pump 224 and 226 is controlled by a respective pump regulator 232 and 234.

The control unit 216 is preferably located in a cabinet 236 together with the pumps 224 and 226 and the water reservoir 218. Also, a heating device 238 is provided in the reservoir 218, under control of a temperature regulator such as a thermostat 240, to maintain the contents of the reservoir 218 at a desired temperature.

In operation, the second embodiment 200 of the invention is used as follows. First, the portion of the patient's body to be treated, for example, an arm, is placed through the flexible flange 206 and into the flexible liner 204 (step S201), and an airtight seal against the skin is achieved. The inflow pump 224 is then started, under control of the control unit 216 (step S202). (More exactly, the operator actuates an external switch, responsive to which the control unit 216 emits necessary signals to activate the inflow pump 224.) Preheated water from the reservoir 218 is pumped through the inflow conduit 228, through the inlet 208 and into the space 242 between the shell 202 and the liner 204. Ordinarily, at the beginning of the process, the liner 204 should preferably lie very close against the inner wall of the shell 202, and consequently, the water is being pumped into a space 242 containing little or no air. As this occurs, the pressure due to the presence of the heated water raises the air pressure in the liner 204 sufficiently to force air out of the liner 204, passing between the arm and the flange 206 (naturally, the seal of the flange against the patient's skin must not be so tight as to prevent this). Alternatively, if desired, a one-way valve could be provided for this purpose, but is not believed to be necessary as a practical matter. As the water rises, it eventually activates the level detector 214, which emits a signal that causes the control unit 216 to activate the outflow pump 226 as well (step S203).

Thus, in this portion of the process, the arm is subjected to a slightly elevated pressure, and is warmed by the heated water.

Once both pumps 224 and 226 are working, the water is pumped in and out of the shell 202 at a constant rate, maintaining the arm or other portion of the body in a steady condition for a predetermined time, under control of the control unit 216. (Alternatively, the duration of this portion of the process could be left to manual control by the operator.) Then, the inflow pump 224 is stopped, while the outflow pump 226 continues to operate, and evacuates the water from between the shell 202 and the liner 204 (step S204). This evacuation of the water reduces the pressure of the air remaining inside the liner 204. The relief valve 212, however, ensures that the pressure inside the shell 202 (and inside the liner 204) does not fall more than a preset amount below ambient atmospheric pressure. In this preferred embodiment, this preset amount or limit is equal to 80 mm of Hg.

This reduction of pressure also results in the flexible flange 206 being forced, by atmospheric pressure, still more tightly against the arm. (If desired, a strap with Velcro (TM) or other fasteners can be used to make this seal still tighter.) At the proper time, the outflow pump 226 is stopped (step S205). Again, this time can be preset in the control unit 216, or the operation of the outflow pump 226 can be stopped by the operator manually. A tourniquet is now placed on the arm, the seal of the flange 206 around the arm is broken, and the patient's arm is removed for venipuncture, intravenous access or the like.

Many variations of the foregoing methods and apparatus are possible without departing from the scope of what the inventors consider to be their invention, broadly construed. For instance, in the first embodiment, instead of one-way valves on the surface of the sleeve or barrier, such valves may instead be provided in a portion (or all) of the lateral surface of the tubular housing. In such case, the heating of the patient's skin is achieved by the conduction of heat through the material of the sleeve, whereas in the arrangement shown, the warming of the skin is partly the result of convection. Also, in all embodiments, the sleeve that receives the limb or other portion of the patient's body may be disposable if for any reason that is desirable. Again, while it is contemplated to provide such sleeve (whether disposable or not), the benefits of the invention may be derived even if no such sleeve is present (at least where no particulate material is used to generate a fluidized bed).

Again, particularly (but not only) in the second embodiment, the inflow pump could be controlled in such fashion as to provide a pulsating action, to provide the limb with a massaging action, as in the first embodiment. Such pulsation could be delivered during part or all of the treatment.

Also, the arrangement of the components on and in the cart 104 may be varied in any convenient manner. One useful variation may be to mount the tubular housing such that its position and orientation can be varied according to convenience. Again, the apparatus need not be mounted on a cart at all. For example, it could be mounted on the wall of a room, or mounted to the interior of an ambulance or the like, or could be constructed to be detachably mountable to a bed, or could be provided without a permanent mounting.

It is also to be understood that the method of the invention, although described above with reference to two preferred embodiments of the apparatus of the invention, could be performed with other, quite different apparatus. Such use of other apparatus to perform the method of the invention, as set out hereafter in the claims, is also within the scope of the invention, with whatever apparatus it may be performed.

As discussed above, with regard to the first embodiment, the blower and suction unit can be separate units or a combined unit having both functions. As a further variation, it is contemplated to use separate units for the blower and the suction source, and in particular to use as the blower a unit such as those conventionally used to provide heated air to a patient covered with a plastic blanket (such arrangements are used conventionally to prevent hypothermia during or after surgery, for example). In this variation, an adapter is provided to fit such blower, the suction source and the tubular assembly containing the chamber to which both suction and blown air are applied. One example of a structure for such an adapter might be a three-way connector made of polyvinyl chloride tubing, or the like. In this variation, or embodiment, also, the tubular assembly can if desired contain particulate matter, so as to utilize a fluidized bed as in the first embodiment, or the particulate material can be omitted. In any event, the successive steps involving the supply of heated fluid (in this case, air) to the chamber followed by application of suction after termination of the supply of heated fluid, may be performed as with the other structures described herein.

Again, while it is most preferably conceived that the invention will be used by insertion of a limb of a patient into the sleeve, the apparatus may be constructed on any scale desired. For example, the sleeve could be constructed large enough to receive the entire lower portion of a patient's body, including part or even the entire torso, and used to stimulate blood flow over a large portion of the body.

Finally, while it is contemplated that the present invention will be used with human patients, veterinary use is also within the scope of the invention.

While the present invention has been described with specific reference to the presently preferred embodiments and variations thereof, which constitute the inventor's best contemplated mode of practicing the invention, many additional modifications and variations thereof will now be readily apparent to those of skill in the art. Accordingly, it is to be understood that the scope of the present invention is to be limited, not by the details of the foregoing illustrative embodiments, but only by the terms of the appended claims.

What is claimed is:

1. A vein dilation device, comprising:
   a chamber having an interior for receiving a portion of a body, said chamber having at least one inlet for admitting a fluid into said chamber;
   a fluid supply connected to said at least one inlet, to enable the fluid to be supplied into said chamber via said at least one inlet;
   a suction source connected to said chamber to apply suction to said interior of said chamber;
   a heater positioned to be able to heat the fluid being supplied into said chamber by said fluid supply; and
   a control system constructed such as to enable said vein dilation device to be operated by actuating said heater and said fluid supply to cause heat to be applied to the portion of the body at a first time, said heater and/or fluid supply are then controlled to terminate application of heat to the portion of the body, after which said suction source is actuated to apply suction to the portion of the body at a second time after termination of the heating.

2. A device according to claim 1, further comprising a control unit that controls at least one of (1) heating of the fluid by said heater, (2) supplying of the fluid into said chamber, and (3) application of suction to said interior of said chamber by said suction source.

3. A device according to claim 1, having a pump for pumping a liquid from a reservoir into said chamber, said pump serving as said fluid supply.

4. A device according to claim 3, having a second pump for pumping the liquid out of said chamber, said second pump serving as said suction source.

5. A vein dilation device, comprising:
   a chamber having an interior for receiving a portion of a body, said chamber having at least one inlet for admitting a fluid into said chamber;
   a fluid supply connected to said at least one inlet, to enable the fluid to be supplied into said chamber via said at least one inlet;
   a suction source connected to said chamber to apply suction to said interior of said chamber; and
   a heater positioned to be able to heat the fluid being supplied into said chamber by said fluid supply, and
   having a blower/vacuum pump which serves as both said fluid supply and said suction source.

6. A method of vasodilation for a portion of a human or other body, comprising the steps of:
   positioning the portion of the body in a sleeve;
   massaging the portion of the body by managing movement of a wall of the sleeve and heating the portion of the body during the massaging; and
   applying a vacuum to the portion of the body after performance of said massaging and heating step.

7. A method of vasodilation for a portion of a human or other body, comprising the steps of:
   positioning the portion of the body in a chamber;
   supplying heat to the portion of the body; and
   after termination of said supplying step, applying vacuum suction to the portion of the body.

8. A method according to claim 7, wherein said supplying step is performed by introducing a heated fluid into the chamber containing the portion of the body.

9. A method according to claim 8, wherein said supplying step is performed by pumping the fluid into the chamber, and said applying step is performed by pumping the fluid out of the chamber such as to place an interior of the chamber at a pressure below ambient atmospheric pressure.

10. A method according to claim 9, wherein, during said supplying step, the pumping of the fluid into the chamber causes air in the space containing the portion of the patient's body to be evacuated from that space, such that during said applying step, the pumping of the fluid out of the chamber causes pressure in the space to be at lower than ambient atmospheric pressure.

* * * * *